United States Patent [19]
Hall

[11] Patent Number: 5,389,347
[45] Date of Patent: Feb. 14, 1995

[54] BIO-HAZARDOUS WASTE STERILIZER AND COMPACTOR

[75] Inventor: John L. Hall, Tracy, Calif.

[73] Assignee: Bromac Enterprises, Tracy, Calif.

[21] Appl. No.: 130,189

[22] Filed: Oct. 1, 1993

[51] Int. Cl.[6] ............................................. A61L 2/04
[52] U.S. Cl. .................................. 422/307; 241/606; 422/308; 422/309
[58] Field of Search ............... 422/307, 308, 309, 269, 422/273, 285, 286, 287; 241/606; 110/223

[56] References Cited

U.S. PATENT DOCUMENTS

| | | | |
|---|---|---|---|
| 2,731,208 | 1/1956 | Dodd | 241/606 X |
| 3,589,276 | 6/1971 | Swallert | 241/606 X |
| 3,881,408 | 5/1975 | Valor . | |
| 4,201,128 | 5/1980 | Whitehead et al. | 422/307 X |
| 4,374,491 | 2/1983 | Stortroen et al. | 422/300 X |
| 4,618,103 | 10/1986 | Wilson et al. | 241/606 X |
| 4,809,915 | 3/1989 | Koffsky et al. | 241/606 X |
| 5,084,250 | 1/1992 | Hall | 422/292 |
| 5,089,228 | 2/1992 | Meijer | 422/37 |
| 5,119,994 | 6/1992 | Placzek | 422/309 X |
| 5,294,412 | 3/1994 | Orlando | 422/295 |

Primary Examiner—Robert J. Warden
Assistant Examiner—Krisanne M. Thornton
Attorney, Agent, or Firm—Harris Zimmerman

[57] ABSTRACT

Hospital wastes or the like are sterilized and compressed for disposal by apparatus having a waste receptacle with a waste receiving opening at the top and having a sterilizer casing, the receptacle and casing being in telescoping relationship. The receptacle initially protrudes from the casing in order to receive the wastes and is then translated into the casing to close the casing and thereby enable sterilization of the contents by admission of pressurized steam. A helical rotary conveyer extends along the axis of the receptacle and has several functions. The conveyer moves wastes from the receptacle into the casing and precompacts such wastes prior to the sterilization cycle and may be used to stir the wastes during sterilization. After opening of a casing door, the conveyer operates to discharge the sterile wastes from the casing and a translatable ram forces the material into an adjacent compactor container.

16 Claims, 4 Drawing Sheets

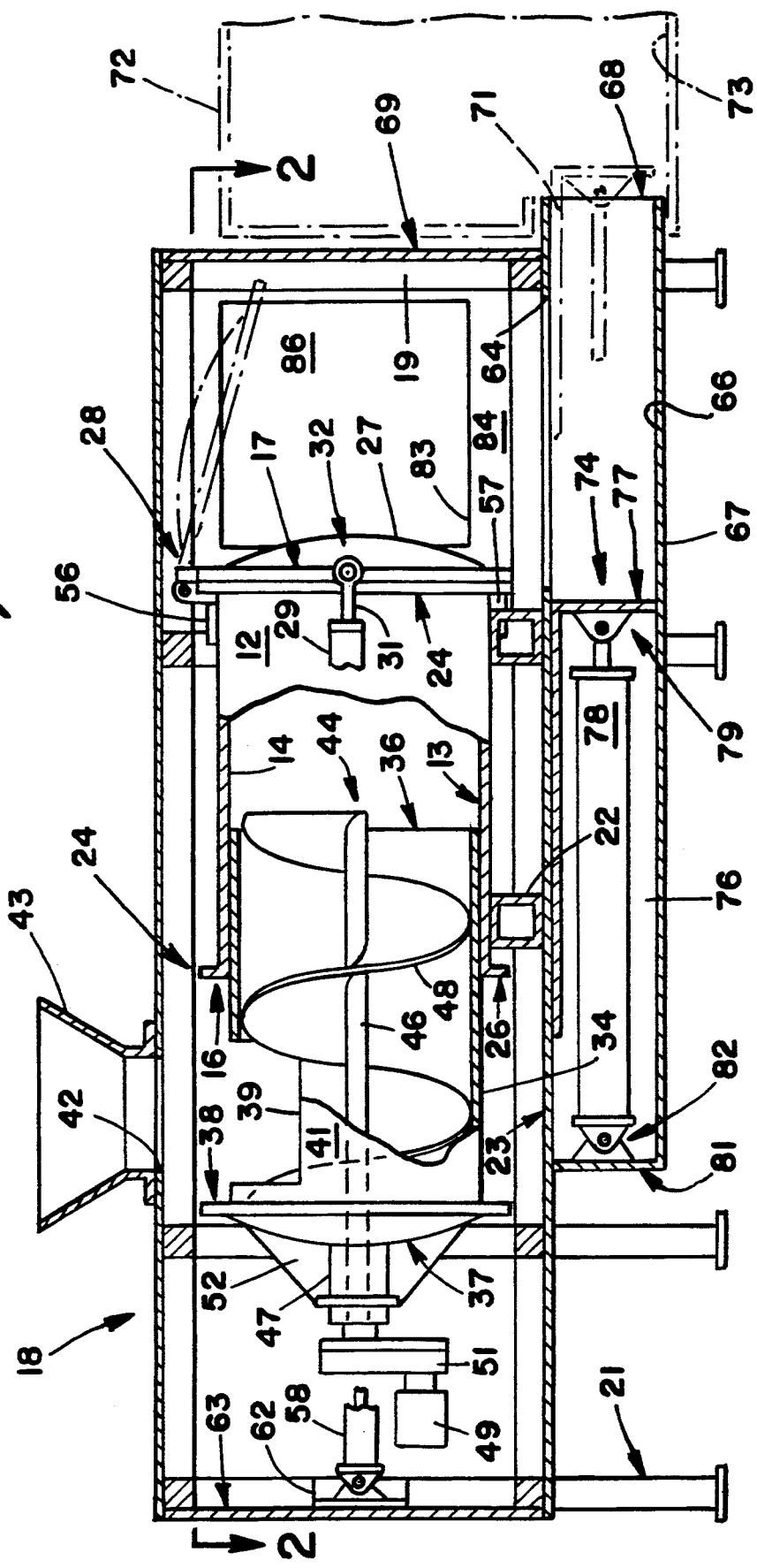
FIG_1

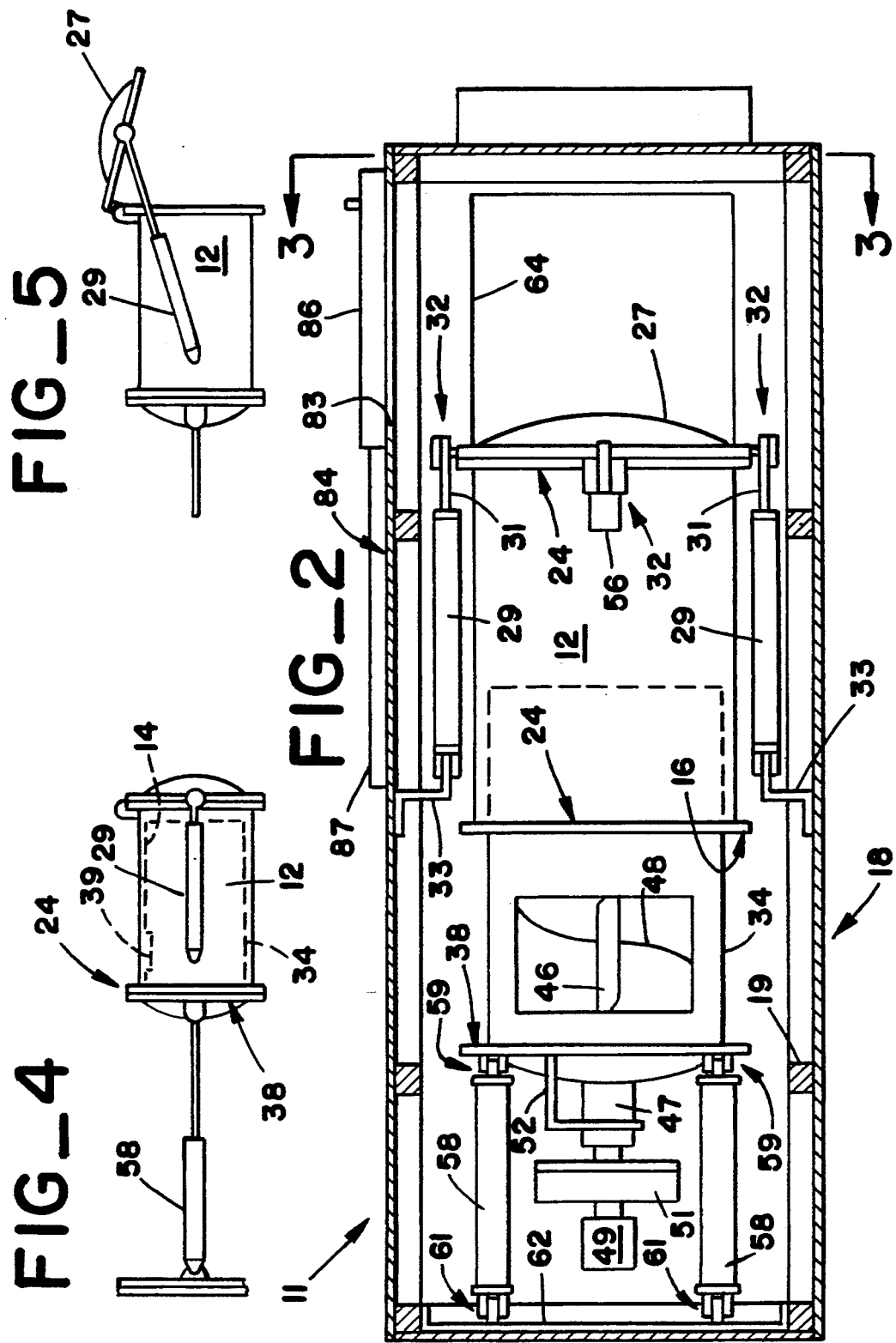

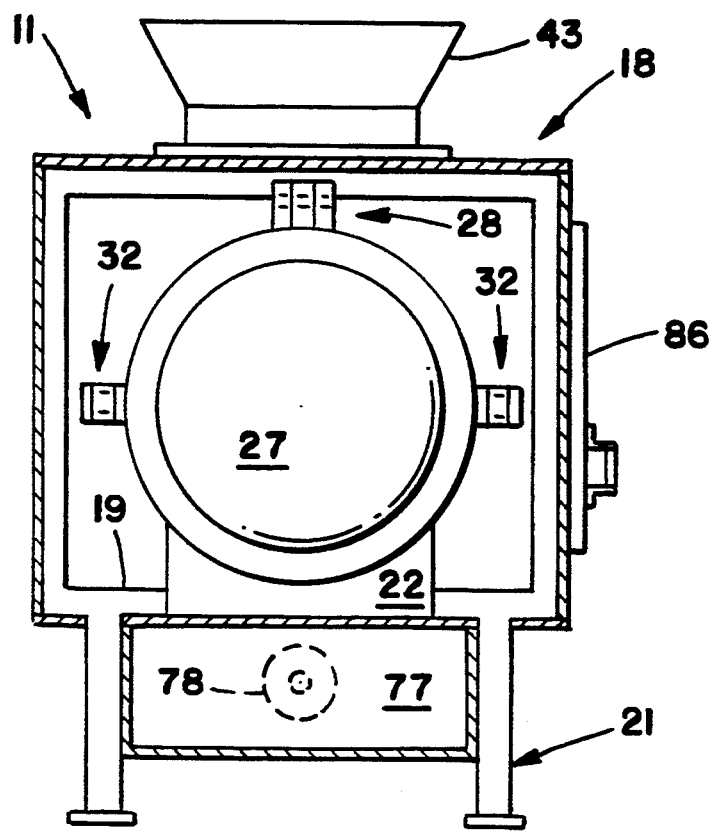
FIG_3
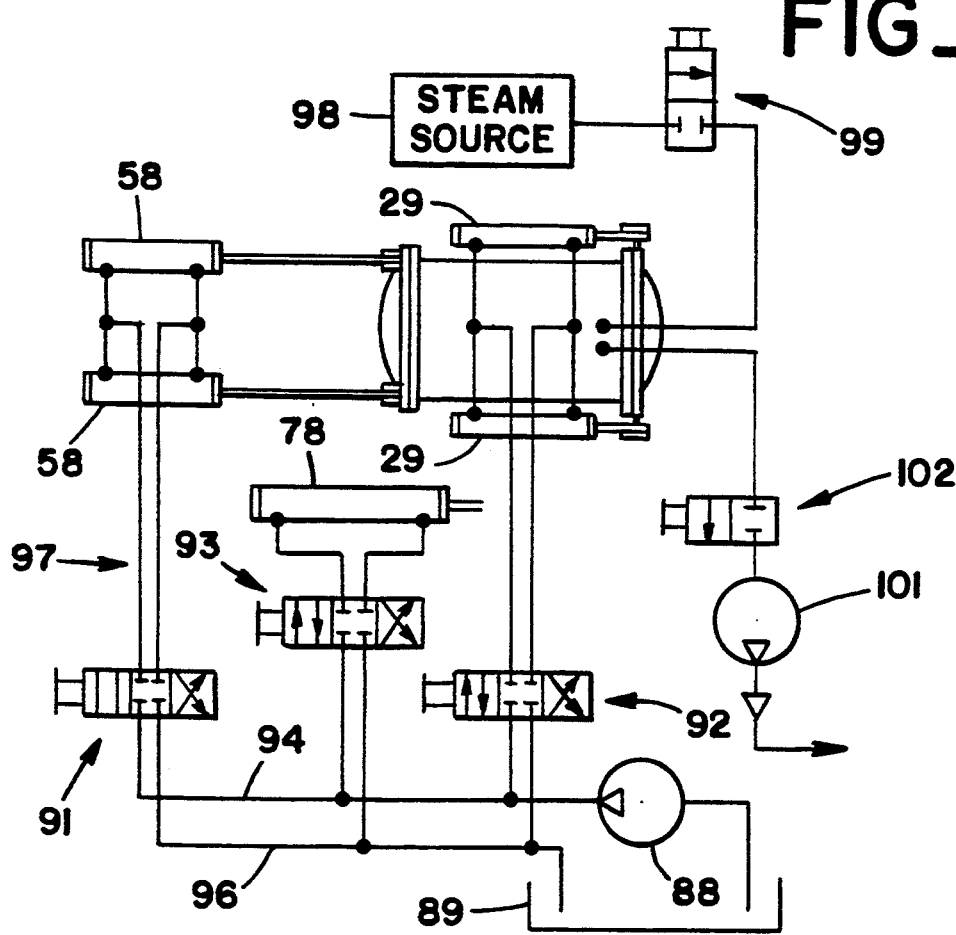
FIG_7

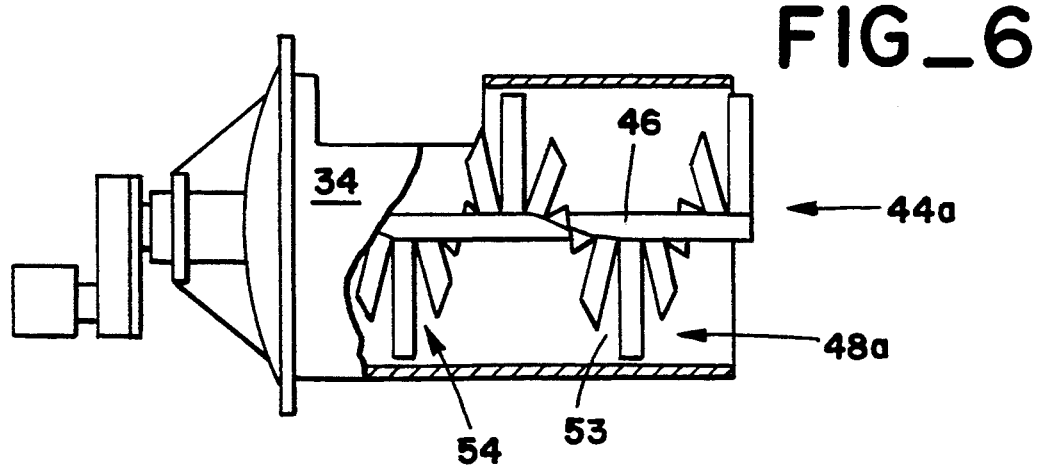
FIG_6
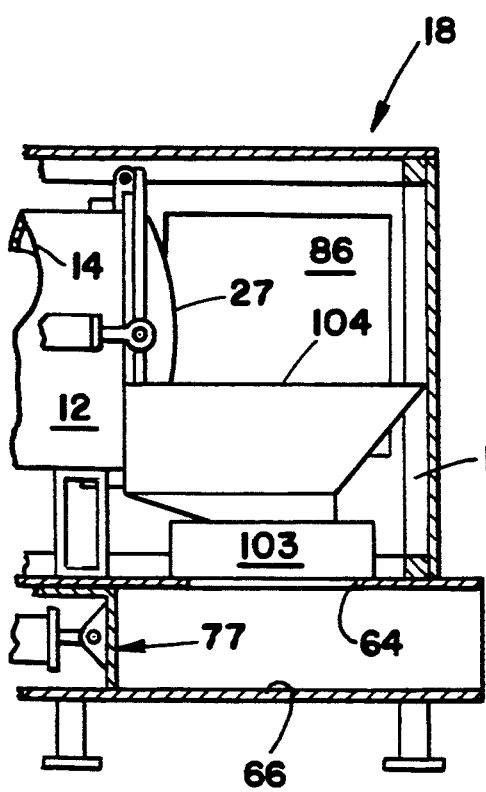
FIG_8
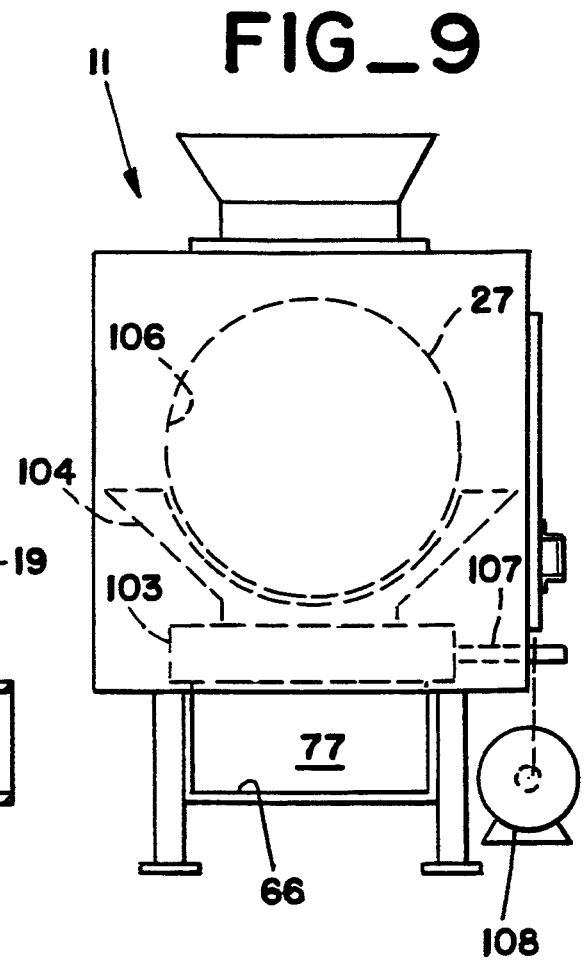
FIG_9

BIO-HAZARDOUS WASTE STERILIZER AND COMPACTOR

TECHNICAL FIELD

This invention relates to the processing of wastes which may be infectious and more particularly to apparatus for receiving, sterilizing and compacting wastes prior to disposal thereof.

BACKGROUND OF THE INVENTION

Hospitals, biological research laboratories and a number of other facilities generate waste materials that may be infectious and therefore cannot be handled in the same manner as ordinary wastes. Bandages, tissues, hypodermic needles and specimen containers are examples of such wastes.

Bio-hazardous wastes of this kind should be stored in closed containers, should not be directly handled by persons and should be sterilized before being disposed of in land-fills or other disposal sites.

Sterilization of such materials by incineration requires costly processing installations because of high fuel costs, pollution problems and other factors. It is simpler and more economical to sterilize the wastes by exposure to steam. Wastes from hospitals and the like are usually compressible and further economies can be realized by compacting the material following sterilization. This enables storage and hauling of greater amounts of the waste in containers and trucks of given capacity and also makes more efficient use of dump-site space.

Prior U.S. Pat. Nos. 5,084,250 and 4,374,491 disclose prior apparatus for temporarily storing, sterilizing and subsequently compacting wastes of the above discussed type before the material is transported to a disposal site. As heretofore constructed, such apparatus typically includes a housing having a sealable internal chamber which can be accessed through a door in the side of the housing when wastes are to be deposited in the chamber. After a sizable amount of such waste has been accumulated, the chamber is sealed, air is evacuated and pressurized steam is admitted to heat the contents to temperatures which destroy biological organisms. The sterile wastes are then discharged from the sterilization chamber and a translatable compactor ram forces the material into the inlet opening of a closed compactor container which is situated adjacent to the apparatus and which, when full, is used to haul the processed waste to a dump-site.

The waste materials are typically contained within disposable plastic bags which initially serve as liners for waste receptacles in the hospital or the like. The contents of the bags are not emptied into the sterilization chamber. The bags are also contaminated waste and are deposited in the chamber with contents intact. The presence of the bags, which may contain much air, and the compressible nature of much of the waste itself results in a low packing density of material in the chamber. This adversely affects operating costs by requiring frequent sterilization cycles and by limiting the amount of waste that is processed during each such cycle. It would be advantageous if the effective capacity of a chamber of given size could be increased.

Sterilization of the waste depends to some extent on the conduction of heat within the mass of waste material as the steam may not directly contact all infectious organisms within the waste. It would be advantageous to provide for a more rapid distribution of heat to all portions of the waste.

It would also be advantageous to facilitate the use of cart dumping machinery for loading wastes into apparatus of the above described kind. Cart dumpers of the known kinds typically lift a cart of wastes and then invert the cart to drop the contents into a hopper or other opening at the top of the waste receiver. The side opening access doors of prior waste sterilizing and compacting apparatus are not conducive to use of such dumping equipment. Moving the access door to the top of the apparatus would enable top loading but would not, in and of itself, increase the effective waste storage capacity of the sterilization chamber.

The present invention is directed to overcoming one or more of the problems discussed above.

SUMMARY OF THE INVENTION

In one aspect, the invention provides apparatus for receiving, sterilizing and compacting hazardous waste material which apparatus has a sterilizing chamber for receiving the material, means for heating the contents of the chamber to a temperature which destroys hazardous organisms and means for compacting the sterilized waste material. The sterilizing chamber casing has a waste entry opening at one end and a waste discharge opening at the other end and a door is situated at the discharge opening. A translatable waste receptacle has an open end and a closed end and a wall with a waste receiving opening, the open end of the receptacle being proportioned for entry into the in sterilizing chamber casing through the waste material entry opening of the casing. The receptacle is translatable between a first position at which the waste receiving opening of the receptacle is outside of the sterilizing chamber and a second position at which it is inside the chamber and at which the receptacle closes the waste material entry opening of the chamber casing. Motor driven feeding means urge waste material which is received in the receptacle towards the other end of the sterilizing chamber casing.

In another aspect, the invention provides apparatus for receiving, sterilizing and compacting hazardous waste material which includes a housing having a processed waste receiving compartment with a waste material ejection opening adapted for communication with a compactor container inlet. A translatable compactor ram is positioned to force waste material out of the receiving compartment through the ejection opening. A sterilizer casing has a waste entry end and a waste discharge end that is positioned to release sterilized waste material into the processed waste receiving compartment of the housing. A substantially cylindrical waste receptacle has a closed end and an open end and a cylindrical wall, a waste receiving opening being located at the top of the wall in proximity to the closed end of the receptacle. The receptacle has a diameter which substantially conforms with the diameter of the inner wall of the sterilizer casing and the receptacle and the casing are in coaxial relationship. The receptacle is translatable in an axial direction between a first position at which the waste receiving opening of the receptacle is outside of the sterilizer casing and is positioned to receive material and a second position at which the opening is inside the casing and at which the waste entry end of the casing is closed by the the closed end of the receptacle. A motor driven helical conveyer is disposed within the receptacle and extends from the closed end of the receptacle towards the waste discharge end of the casing and has a diameter which conforms substantially to the diameter of the receptacle and a length which corresponds substantially to the length of the casing. A door enables opening and closing of the waste discharge end of the casing. Means are provided for admitting pressurized steam into the casing and receptacle when the door is closed and the receptacle is at its second position.

The invention enables more efficient processing of infectious wastes in part by providing feeding mechanism which precompacts the wastes in the course of feeding the wastes into the sterilizing chamber. This enables processing of a greater amount of waste in a sterilizing chamber of given size during each sterilization cycle. The same mechanism may be used to stir or mix the wastes during the sterilization process to provide for a more uniform heating of the mass and also serves to eject the wastes from the sterilization chamber at the end of the process. The invention is particularly advantageous where wastes are dropped into a hopper or the like at the top of the apparatus. Wastes which would otherwise pile up directly beneath the hopper are moved away from the hopper by the feeding mechanism thereby enabling input of still more wastes.

The invention, together with further aspects and advantages thereof, may be further understood by reference to the following description of the preferred embodiments and by reference to the accompanying drawings.

BRIEF DESCRIPTION OF THE DRAWINGS

FIG. 1 is an elevation section view of apparatus for receiving, sterilizing and compacting waste material, portions of certain components being broken out in order to expose internal structure.

FIG. 2 is a plan section view of the apparatus of FIG. 1 taken along line 2—2 thereof.

FIG. 3 is a cross section view of the apparatus of the preceding figures taken along line 3—3 of FIG. 2.

FIG. 4 is a side view of the waste receptacle and sterilizing chamber components of the apparatus shown in a closed and sealed condition.

FIG. 5 is another side view of the waste receptacle and sterilizing chamber components as they appear when opened to enable discharge of the sterilized waste.

FIG. 6 is an elevation section view of a modified form of waste receptacle which can replace the corresponding component of the apparatus of the preceding figures.

FIG. 7 is a a fluid circuit diagram depicting components for controlling the apparatus of the preceding figures.

FIG. 8 is an elevation section view of the waste discharging end of another embodiment of the apparatus as modified to produce shredded wastes.

FIG. 9 is an end view of the embodiment of FIG. 8.

DETAILED DESCRIPTION OF THE PREFERRED EMBODIMENTS

Referring initially to FIGS. 1, 2 and 3 of the drawings, the infectious waste processing apparatus 11 of this embodiment of the invention has a tubular sterilizer casing 12 with a cylindrical inner surface 13 that bounds the sterilizing chamber 14. The casing 12 extends horizontally and has a waste entry end 16 and an opposite waste discharge end 17. The casing 12 is preferably disposed within an enclosing housing 18 which has an internal frame 19 that reinforces the structure and which is supported by legs 21. Casing support members 22 position the casing 12 above the housing floor 23.

To provide for sealing of the chamber 14, each end 16 and 17 of casing 12 has an annular outwardly extending flange 24 carrying an annular compressible seal 26. A circular pressure door 27 enables opening and closing of the waste discharge end 17 of casing 12. The door 27 is hinged to the casing 12 by a pivot coupling 28 at the top of the door and thus may be swung outward and upward from the end 17 of the casing to enable discharge of sterilized wastes from the casing. Opening and closing of door 27 is effected by a pair of fluid cylinders 29 of the known kind which have extendible and retractable rods 31. The cylinders 29 are disposed at opposite sides of casing 12 and the rods 31 are coupled to the door 27 by pivot couplings 32 situated at opposite sides of the door. The head ends of cylinders 29 are pivoted to brackets 33 which are secured to housing 18.

An axially translatable waste receptacle 34 of tubular configuration has a diameter which conforms with the diameter of the sterilizing chamber 14 and is disposed in coaxial, telescoping relationship with casing 12. The end 36 of receptacle 34 that is within casing 12 is open and the opposite end 37 of the receptacle is closed and has an annular flange 38 that conforms with the flange 24 at the corresponding end 16 of the casing. A waste receiving opening 39 is provided in the cylindrical wall 41 of the receptacle at a location which is at the top region of the wall and which is close to the closed end 37 of the receptacle.

Receptacle 34 has a waste receiving position, shown in FIGS. 1 and 2, at which it protrudes from end 16 of casing 12 for a distance that is sufficient to situate the waste receiving opening 39 outside of the interior of the the casing in position to receive wastes which are dropped though a conforming opening 42 in the ceiling of housing 18. A hopper 43 above opening 42 facilitates depositing of the wastes which operation can be performed by a cart dumper or other motor driven materials handling equipment of one of the known forms as the waste material entry is at the top of the apparatus 11.

The receptacle 34 carries motor driven feeding means 44 for urging the waste material towards the remote end 17 of casing 12. This prevents a rapid pile up of material directly below opening 39 that might otherwise block entry of still more material and also effects an initial precompaction of the wastes within the sterilizing chamber 14 thereby enabling treatment of a greater amount of material during each sterilizing cycle.

The feeding means 44 of this embodiment is a helical rotary conveyer of the auger or screw type. A rotatable shaft 46 extends along the axis of the cylindrical receptacle 34 from a support bearing and seal 47 at the center of the closed end 37 of the receptacle. The shaft 46 carries a helical blade 48 which extends along the shaft and which preferably has a diameter that conforms with the inner diameter of the receptacle. The shaft is rotated by an electrical drive motor 49 which is coupled to the shaft through a speed reducing gearbox 51. The bearing 47 and the motor 49 and gearbox 51 are supported by a bracket 52 which extends from the closed end 37 of receptacle 34.

The blading on shaft 46 may have other configurations. As shown in FIG. 6, for example, the blade means 48a may be a series of vanes 53 which extend radially from shaft 46 at successive locations along the shaft and which collectively form a helical conveyer having openings 54 between successive vanes. This configuration is advantageous for processing certain types of material, such as animal bedding for example, as it acts to shred and stir the material during the sterilizing operation.

Referring again to FIGS. 1, 2 and 3, the shaft 46 and blade 48 preferably have a length that corresponds to the length of casing 12 to enable stirring of all portions of the contents of chamber 14 during the sterilization cycle. The length of receptacle 34 is slightly shorter than the length of casing 12 to avoid obstruction of a steam inlet fitting 56 at the top of the casing and a condensate outlet fitting 57 at the base of the casing which fittings are at the waste discharge end 17 of the casing.

When the chamber 14 and receptacle 34 have been filled, the receptacle is translated further into casing 12 to the position shown in FIG. 4 at which flange 38 of the receptacle bears against the flange 24 at the adjacent end of the casing. This moves the waste receiving opening 39 of the receptacle 34 into the interior of casing 12 and acts to close and seal the sterilization chamber 14. The feeding means 44 is operated during translation of the receptacle 34 and further compaction of the waste material occurs during such translation.

Referring again to FIGS. 1, 2 and 3, translation of the waste receptacle 34 is effected by another pair of fluid cylinders 58 which have rod ends coupled to the closed end 37 of the receptacle by a pair of pivot couplings 59 that are situated at opposite sides of the receptacle. Another pair of pivot couplings 61 couple the head ends of the cylinders 58 to a brace 62 that extends across the housing 18 at the inner surface of the adjacent end wall 63 of the housing and which is secured to the housing framework 19.

Following the translation of receptacle 34 which closes and seals chamber 14, pressurized steam is directed into the chamber for a period of time sufficient to destroy bio-hazardous organisms in the waste. The temperature, pressure and duration of the sterilization cycle may vary depending on the composition of the wastes. All types of waste can be made non-infectious by a 30 minute exposure to steam having a temperature of 280° F. and a pressure in the range from 37 to 40 pounds per square inch.

It preferable, but not essential in all instances, that air be evacuated from the chamber 14 prior to the introduction of steam as this results in a more rapid heating of the contents. Apparatus for this purpose will be hereinafter described.

The feeding means 44, 44a may be operated during the sterilizing cycle to stir or mix the waste material and thereby cause a more rapid and uniform heating of the wastes. This enables agitation of the waste to facilitate sterilization of dense materials such as animal bedding in laboratory infectious waste for example.

Following the sterilization cycle, fluid cylinders 9 are actuated to pivot door 27 outward and upward to the position shown in FIG. 5. Referring again to FIGS. 1, 2 and 3, the feeding means 44 then operates to eject the sterilized wastes from chamber 14. The ejected wastes fall through an opening 64 in the floor 23 of housing 18 and into a processed waste receiving compartment 66 which is situated below the floor.

Compartment 66 is formed by a channel member 67 which extends along the underside of the housing floor 23. An open end 68 of the channel member 67 protrudes a short distance outward from the overlying end wall 69 of housing 18 and has a rectangular configuration proportioned to enter into the waste inlet 71 of an adjacent compactor container 72. The compactor container 72 may be of the known type which forms a closed chamber 73 for receiving wastes and which is used to transport compacted wastes to a dump site.

Sterilized wastes which drop into compartment 66 are forced into the container 72 by a translatable compactor ram 74. Ram 74 has an inverted channel shaped ram member 76 having a height and width conforming with the height and width of of the interior of channel member 67 and has an end wall 77 which faces the open end 68 of channel member 67. The ram member is translatable along channel member 67 between an inactive position shown in solid lines in FIG. 1 and an extended position, shown in dashed lines, at which the end wall 77 of the ram member is within the adjacent compactor container 72. The ram member 76 blocks movement of waste material through the housing floor opening 64 when the ram is at the extended position but does not obstruct such movement when at the inactive position.

Translation of the ram member 76 between the inactive and extended positions is effected by another fluid cylinder 78 situated in channel member 67 and which extends into the ram member 76. The extendible and retractable rod of cylinder 78 is coupled to the back of the ram member end wall 77 by a pivot coupling 79 and the head end of the cylinder is pivoted to a closed end wall 81 of channel member 67 by another such coupling 82.

As the compactor container 72 is closed, repeated translations of the ram 74 act to fill the container with loosely packed waste and thereafter act to compact or compress the waste by forcing still more material into the container.

Following the sterilization and compaction cycles described above, door 27 is reclosed by contracting fluid cylinders 29 and waste receptacle 34 is translated by cylinders 58 to re-locate the waste receiving opening 39 under hopper 43. The apparatus 11 is then in condition for receiving and processing additional waste material.

Hospitals or the like typically generate non-hazardous wastes as well as infectious wastes. Sterilization of the non-hazardous wastes increases operating costs without providing any benefit. An opening 83 in a side wall 84 of housing 18 is situated above the waste receiving compartment 66 to enable direct deposit of non-hazardous wastes in the compartment without subjecting such wastes to the sterilizing process. An access door 86, which is slidable along rails 87, closes opening 83 except at times when non-hazardous waste is being deposited.

Referring to FIG. 7, a pump 88 provides pressurized hydraulic fluid for operating the fluid cylinders 29, 58 and 78. Pump 88 draws fluid from a reservoir 89 and delivers the fluid to each of three cylinder control valves 91, 92 and 93 though an outlet conduit 94. A drain conduit 96 returns fluid from each of the control valves 91, 92 and 93 to reservoir 89. Control valve 91 has two outlet lines 97 which are communicated with opposite ends of the receptacle translating cylinders 58. The control valve 91 has a first position at which fluid is supplied to the head ends of the cylinders 58 and vented from the rod ends of the cylinders to extend the cylinders. At a second position of valve 91, both outlet lines 97 are blocked thereby immobilizing the cylinders 58. A third position of the control valve 91 causes contraction of the cylinders 58 by transmitting fluid to the rod ends of the cylinders and by venting the head ends to drain conduit 96. Control valves 92 and 93 control the door operating fluid cylinders 29 and the compactor ram fluid cylinder 78 in a similar manner.

Steam from a suitable source 98 is transmitted to the inlet fitting 56 of sterilizer casing 12 through a flow control valve 99. Many hospitals have a pre-existing steam supply which can be utilized in the operation of the present apparatus. In other instances, the source 98 may include a boiler. To enable evacuation of air from the sterilization chamber, the intake of a vacuum pump 101 is communicated with the chamber through a flow control valve 102 and the previously described condensate drain fitting 57. Pump 101 may be of the aspirator type that can be operated by a flow of steam from source 98. Valve 102 may be adjusted to establish a controlled outflow of steam from the sterilization chamber to enable inflow of steam at a rate sufficient to maintain the desired temperature.

Some types of waste material can be compacted to a greater degree than is otherwise the case if the material is shredded or milled into small fragments. Referring jointly to FIGS. 8 and 9, this may be accomplished by disposing a shredder 103 within the housing 18 above the compactor inlet opening 64 in position to intercept the waste material that is discharged from the sterilization chamber 14 and to release the shredded material into the waste material receiving compartment 66. The shredder 103, which may otherwise be of one the known designs, has an intake hopper 104 of sufficient size to intercept all material that is ejected from sterilization chamber 14 and which extends a distance above the base of the chamber. The side of hopper 104 which abuts the end of the sterilizer casing 12 has an arcuate notch 106 which conforms with the periphery of the casing and thus the hopper does not obstruct the discharge of material from the casing.

The drive shaft 107 of shredder 103 extends out of housing 18 and is coupled to a drive motor 108 located outside of the housing. The frame 19 of housing 18 is of greater vertical extent than in the previously described embodiments. This provides for a greater vertical spacing between the sterilizer casing 12 and the processed waste material receiving compartment 66 to accommodate to the presence of the shredder 103. The apparatus may otherwise be similar to one of the previously described embodiments.

While the invention has been described with reference to certain specific preferred embodiments for purpose of example, many modifications and variations of the apparatus are possible and it is not intended to limit the invention except as defined in the following claims.

I claim:

1. Apparatus for receiving, sterilizing and compacting hazardous waste material which apparatus has a sterilizing chamber for receiving said waste material, means for heating the contents of said chamber to a temperature which destroys hazardous organisms in said waste material and means for compacting waste material which has been processed in said sterilizing chamber, wherein the improvement comprises:

a sterilizer casing forming said sterilizing chamber and having a waste material entry opening at one end of said chamber and a waste discharge opening at the opposite end thereof, a door at said opposite end of said sterilizer casing, said door being movable between a closed position at which said waste discharge opening is closed and an open position at which waste material may be discharged from said chamber through said discharge opening, a translatable hollow waste receptacle having a wall with a waste receiving opening therein and having an open end and a closed end, said receptacle being proportioned for entry of said open end thereof into said sterilizing chamber through said waste material entry opening thereof, said receptacle being translatable between a first position at which said waste receiving opening in said receptacle wall is situated outside of said sterilizing chamber to enable deposit of wastes in said receptacle and a second position at which said waste receiving opening is inside said sterilizing chamber and at which said receptacle closes said waste material entry opening of said sterilizer casing, and motor driven feeding means for urging waste material which is received in said receptacle towards said opposite end of said sterilizer casing.

2. The apparatus of claim 1 wherein said motor driven feeding means extends within said hollow translatable waste receptacle and is carried thereby and is translatable therewith.

3. The apparatus of claim 1 wherein said motor driven feeding means includes a rotatable shaft extending towards said opposite end of said sterilizing chamber from said closed end of said translatable receptacle within said receptacle and being translatable therewith and being rotatable relative thereto, a rotary motor coupled to said shaft to turn said shaft and at least one blade which extends radially from said shaft, said blade being angled relative to said shaft in order to urge waste material towards said opposite end of said sterilizing chamber as said shaft rotates.

4. The apparatus of claim 3 wherein said blade is a helical auger blade extending along said shaft and being positioned to intercept waste material which is entered into said waste receiving opening of said receptacle when said receptacle is at said first position thereof and which extends within said sterilizing chamber when said receptacle is at said second position thereof.

5. The apparatus of claim 3 wherein said motor driven feeding means includes a plurality of said blades which are positioned to intercept waste material which is entered into said waste receiving opening of said receptacle when said receptacle is at said first position thereof, said blades of said plurality thereof being at different locations along the length of said shaft and having outer ends which are spaced apart from each other.

6. The apparatus of claim 3 wherein said wall of said receptacle has an inner surface of substantially cylindrical configuration and wherein said rotatable shaft extends in coaxial relationship with said inner surface and wherein said blade extends outward from said shaft for a distance that conforms substantially with the radius of said cylindrical surface.

7. The apparatus of claim 1 wherein said receptacle is of substantially cylindrical configuration and wherein said sterilizer casing has a cylindrical inner wall with a diameter that conforms substantially with the diameter of said receptacle, said receptacle and sterilizer casing wall being in coaxial relationship.

8. The apparatus of claim 1 wherein said ends of said receptacle are horizontally spaced apart and wherein said wall extends therebetween in a horizontal direction, said waste receiving opening being at the uppermost region of said wall whereby waste materials may be dropped into said receptacle from a location which is above said apparatus.

9. The apparatus of claim 1 wherein said waste material entry opening at said one end of said sterilizing chamber is bounded by an end surface of said sterilizer casing and wherein said closed end of said translatable receptacle has a continuous flange positioned to bear against said end surface when said receptacle is translated to said second position thereof whereby said waste material entry opening of said sterilizing chamber is sealed closed by said receptacle when said receptacle is at said second position thereof.

10. The apparatus of claim 1 further including a shredder situated below said waste discharge opening of said sterilizing chamber in position to receive and shred sterilized waste material which is discharged therefrom prior to entry of said material into said compaction means.

11. The apparatus of claim 1 wherein said sterilizer casing has a cylindrical inner surface that is centered on a horizontally extending axis and wherein said translatable waste receptacle has a conforming cylindrical shape, said casing and receptacle being in a coaxial and telescoping relationship, said waste receiving opening of said receptacle being at the upper portion of said receptacle wall, wherein said feeding means includes a rotatable shaft which extends from said closed end of said waste receptacle along said axis and in the direction of said opposite end of said sterilizing chamber, further including blade means for urging waste materials in the direction of said opposite end of said sterilizing chamber in response to rotation of said shaft which blade means is secured to said shaft and extends therealong from a location that is adjacent said closed end of said waste receptacle to a location that is spaced from said opposite end of said chamber when said receptacle is at said second position thereof by a distance at least equal to the distance that said receptacle travels between said first and second positions thereof.

12. Apparatus for receiving, sterilizing and compacting hazardous waste material comprising:
a housing having a processed waste material receiving compartment with a waste material ejection opening constructed and arranged for communication with a compactor container inlet;
a translatable compactor ram positioned to force processed waste material out of said receiving compartment through said ejection opening;
a sterilizer casing having a cylindrical inner wall surface and a waste entry end and a waste discharge end, said discharge end being positioned to release sterilized waste material into said waste material receiving compartment of said housing;
a substantially cylindrical waste receptacle having a closed end and an open end and a cylindrical wall which extends therebetween and having a waste receiving opening located at the top of said wall in proximity to said closed end of said receptacle, said receptacle having a diameter substantially conforming to the diameter of said inner wall surface of sterilizer casing, said receptacle being disposed in coaxial relationship with said casing, said receptacle being axially translatable along said casing between a first position at which said waste receiving opening is moved outside of said casing and is positioned to receive material and a second position at which said waste receiving opening is moved inside of said casing and at which said waste entry end of said casing is closed by said closed end of said receptacle;
a motor driven helical rotary conveyer disposed within said receptacle for rotation relative thereto and which extends from said closed end thereof towards said waste discharge end of said casing, said conveyer having a diameter which corresponds substantially to the diameter of said receptacle and having a length which corresponds substantially to the length of said casing;
a door at said waste discharge end of said casing, said door being movable to open and close said waste discharge end of said casing; and
means for admitting pressurized steam into said casing and waste receptacle when said door is closed and said receptacle is at said second position thereof.

13. The apparatus of claim 12 further including a shredder disposed below said second end of said casing and above said processed waste material receiving compartment in position to receive and shred material which is discharged from said second end of said casing prior to entry of said material into said compartment.

14. In apparatus for sterilizing bio-hazardous waste which apparatus has a sealable sterilizing chamber in which said waste may be temporarily deposited, said chamber having a first end and an opposite end and a chamber wall extending therebetween which wall has a substantially cylindrical inner surface, said apparatus further having means for sterilizing the contents of said chamber, the improvement comprising:
a rotatable shaft extending within said chamber in coaxial relationship with said cylindrical inner wall surface, at least one blade extending radially from said shaft which blade is angled relative to said shaft in order to urge the contents of said chamber towards said opposite end thereof when said shaft is rotated in a first angular direction, and motor means for rotating said shaft relative to said chamber wall in said first angular direction whereby said waste is compacted within said sterilizing chamber.

15. The apparatus of claim 14 wherein said opposite end of said sterilization chamber against which said waste is compacted is formed at least in part by an openable door.

16. The apparatus of claim 15 wherein said wall of said chamber has a waste entry opening extending therethrough at a region of said wall that is proximal to said first end of said chamber.

* * * * *